United States Patent [19]

Manchand

[11] 4,147,708

[45] Apr. 3, 1979

[54] PREPARATION OF CAROTENOIDS USING A π-ALLYL COMPLEX

[75] Inventor: Percy S. Manchand, Montclair, N.J.

[73] Assignee: Hoffmann-La Roche Inc., Nutley, N.J.

[21] Appl. No.: 793,220

[22] Filed: May 2, 1977

Related U.S. Application Data

[63] Continuation-in-part of Ser. No. 627,435, Oct. 30, 1975, abandoned.

[51] Int. Cl.$^2$ .................. C11C 1/00; C07C 27/00; C07C 43/20

[52] U.S. Cl. ................. 260/413; 260/429 L; 260/607 AR; 260/400; 260/607 AL; 260/410.9 R; 260/402; 260/410.9 V; 560/254; 560/260; 568/875; 568/654; 568/824

[58] Field of Search ............. 260/413, 617 A, 613 D; 560/254, 260

[56] References Cited

U.S. PATENT DOCUMENTS 3,876,673  4/1975  Julia .................................. 260/413

OTHER PUBLICATIONS

"Geometrical Isomerism of π-Allyl Complexes of PdCl$_2$ and Dienes", by O. G. Levanda et al. Zhurnal Organicheskoi Khimii, vol. 7, No. 2, pp. 217-273, Feb. 1971.

*Primary Examiner*—Winston A. Douglas
*Assistant Examiner*—John F. Niebling
*Attorney, Agent, or Firm*—Jon S. Saxe; Bernard S. Leon; George W. Johnston

[57] ABSTRACT

A novel procedure for the preparation of carotenoids, particularly vitamin A, employing π-allyl transition metal complexes. Novel carotenoid intermediates are also disclosed.

13 Claims, No Drawings

PREPARATION OF CAROTENOIDS USING A π-ALLYL COMPLEX

RELATED APPLICATIONS

This is a continuation-in-part of U.S. patent application Ser. No. 627,435, filed Oct. 30, 1975, now abandoned.

BACKGROUND OF THE INVENTION

The present invention relates to the preparation of carotenoids, particularly vitamin A. Although vitamin A is a relatively simple molecule, its construction has presented a formidable synthetic challenge. Prior art procedures for the preparation of vitamin A, as well as other carotenoids, involve extensive functionalization with concomitant stereochemical and stability problems. Other difficulties encountered with prior art syntheses involve coping with unstable reagents and intermediates. The foregoing factors have an adverse effect on the ultimate yield and steric purity of the final vitamin A product.

A very important consideration in the synthetic preparation of carotenoids and other natural products is the recognition of the fact that the isoprene $C_5$ structure is the basic unit of such products. The biogenetic path of these products involves the incorporation of the $C_5$ repeating unit into a large variety of open and ring structures. It is immediately apparent that isoprene represents an obvious choice as a starting material for carotenoid preparation. Attempts to synthesize natural products from isoprene normally require the functionalization of isoprene. Successful functionalizations of isoprene have involved the addition of anhydrous hydrochloride to isoprene yielding a mixture of prenyl chloride and isoprenyl chloride. This and other halogenation type reactions of isoprene are quite limited due to the difficulty of replacing the halogen substituents selectively with other functional groups. Even when the requisite functionalization has been accomplished, there still remain the problems described above.

The process of the instant invention avoids the problems of the prior art by employing π-allyl complexes of transition metals and an isoprene derivative, the latter embodying the alcohol function which is to appear in the final product. The π-allyl complex, described in greater detail hereinafter, is then coupled with a sulfone. The reaction product is further treated to obtain the desired carotene. In the case of vitamin A, the π-allyl complex is coupled with a vinyl-β-ionyl sulfone, prepared in accordance with Julia, U.S. Pat. No. 3,781,313.

In accordance with this invention, vitamin A and other carotenes are obtained in high yields and high steric purity while encountering none of the problems faced by prior art carotene syntheses.

SUMMARY OF THE INVENTION

This invention relates to the preparation of carotenes, particularly compounds of the formulae:

(a) 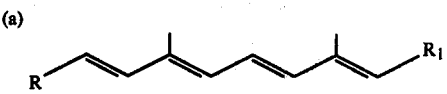 I wherein
R is either of

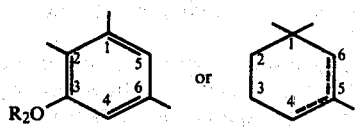

$R_1$ is —CH$_2$OH,

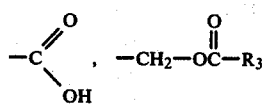

or $CO_2R_6$; $R_2$, $R_3$ and $R_6$ are lower alkyl; the dotted line is a carbon-carbon bond either in the 4,5 or the 5,6-position.

(b) 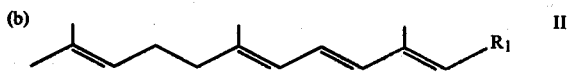 II wherein $R_1$ is as above; and (c) 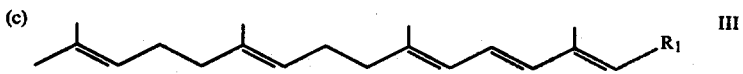 III wherein $R_1$ is as above which comprises reacting a compound of the formula

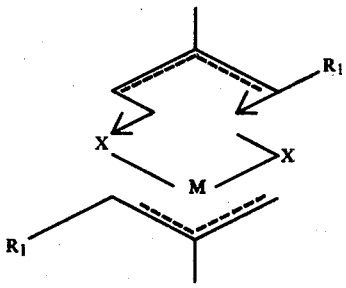 IV wherein M is Pd or Pt, X is halogen and $R_1$ is as above with a compound of the formula:

 V $R_4$—CH$_2$SO$_2$R$_5$ wherein
$R_4$ is

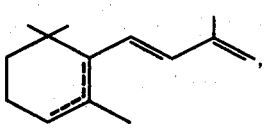 V-A

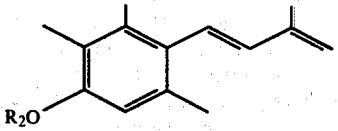 V-B

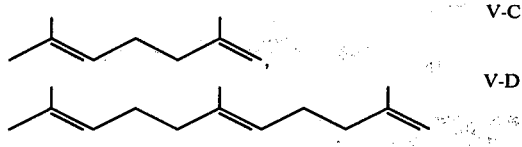

$R_2$ is as above and the dotted line is a carbon-carbon bond which may be in either the 4,5 or the 5,6 position, and $R_5$ is alkyl, aryl, or lower alkylaryl in the presence of a ligand under basic conditions. This reaction may also be carried out by employing, in lieu of ligands, a solvent capable of coordinating with the platinum or palladium, (e.g. dimethylsulfoxide).

DESCRIPTION OF THE INVENTION

As used herein, the term "alkyl" refers to straight or branched chain hydrocarbon groups having from 1-20 carbon atoms, e.g., methyl, ethyl, propyl, butyl, octadecyl and the like. The term "lower alkyl" refers to hydrocarbon chains of the above nature containing from 1-6 carbon atoms. The term "aryl" refers to substituted or unsubstituted mononuclear or polynuclear aryl groups such as phenyl, naphthyl, phenanthryl, azulyl, tolyl, ethylbenzyl and the like. Aryl groups containing substituents such as lower alkyl and lower alkoxy, which groups contain 1-6 carbon atoms, are included within the definition of aryl.

The term "halogen" includes chlorine, bromine, fluorine and iodine. The term "alkali metal" refers to sodium, potassium and lithium. The term "lower alkanol" as used herein refers to an alkanol having 1-6 carbon atoms. The term "$\pi$-allyl complex" refers to a complex formed between a positive metal ion and an unsaturated organic compound, particularly a compound having the allylic structure, wherein the metal ion, while not bonded to a particular carbon, is located on the lobes of two $\pi$electrons.

The preparation of compounds having the structures of formulae I, II or III are prepared by first providing a compound of formula IV. The compound of formula IV is prepared by reacting isoprene according to conventional procedures to obtain compounds of the formulae:

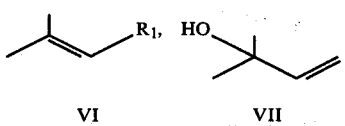

wherein $R_1$ is as above

Compounds VI or VII are then treated with a halide of a transition metal, preferably palladium or platinum in the presence of an organic acid-acid anhydride, an alkali metal halide, buffering agents and oxidizing agents to form a compound of formula IV. The reaction is carried out at a temperature of from 25° C. to about 120° C., preferably about 80° C.

The organic acid-acid anhydrides that may be employed are lower alkyl monocarboxylic acids and the corresponding anhydrides such as acetic acid-acetic anhydride, propionic acid-propionic anhydride and the like. Preferred is acetic acid-acetic anhydride.

As buffering agents there may be employed the alkali metal salts of the aforementioned organic acids. The preferred buffering agent is sodium acetate. The presence of the buffer ensures the formation of the $\pi$-allyl complex.

The alkali metal halides employed in this reaction are preferably the halides of sodium and potassium. Sodium chloride is particularly preferred.

Typical oxidizing agents that may be employed in this reaction are conventional compounds such as the halides of copper, chromium and the like. Cupric chloride is particularly preferred.

The concentration of the aforementioned reactants to compounds VI, or VII is not critical and may vary from about 0.1:1 to about 10:1, on a molar basis, of compound VI or VII to each reactant. Generally, a molar ratio of each reactant to compound VI or VII of about 1:1 is employed.

A particularly preferred compound of formula IV prepared according to the foregoing procedure, is a compound of the formula

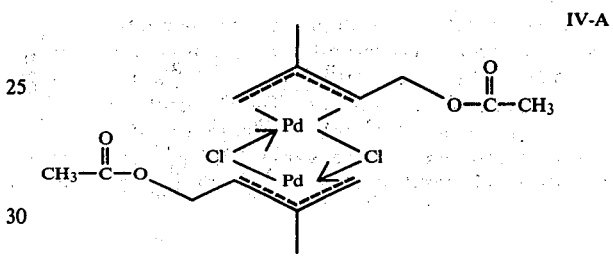

Compound IV-A is novel and provides one aspect of this invention. Compound IV-A is prepared in accordance with the foregoing sequence when prenyl acetate is reacted with palladium chloride, sodium chloride, sodium acetate or cupric chloride in the presence of acetic acid-acetic anhydride. In lieu of prenyl acetate, a compound of formula VII may be employed to form compound IV-A. Prenyl acetate is preferred, however.

When a compound of formula VI where $R_1$ is $CO_2R_6$ is reacted in accordance with the above sequence, employing palladium chloride, there is obtained a compound of the formula

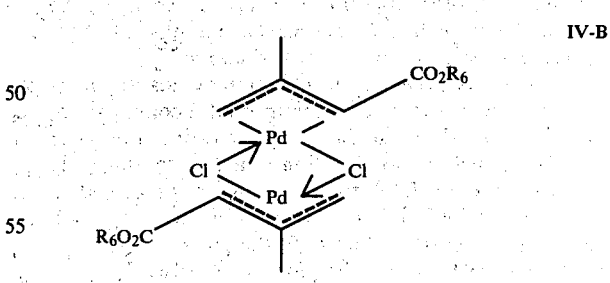

wherein $R_6$ is as above. $R_6$ is preferably methyl.

Compound IV-B is novel and provides another aspect of this invention.

The sulfone of compound V where $R_4$ is either

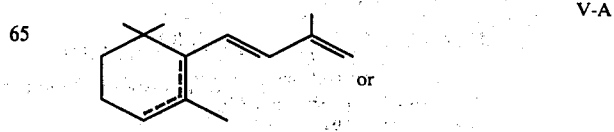

-continued

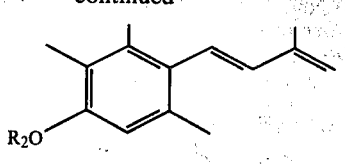
V-B where the dotted line is a carbon-carbon bond in either the 4,5 or 5,6 position;

is prepared by treating compounds of the formula

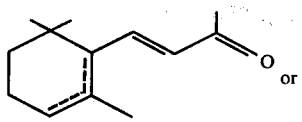
VIII or

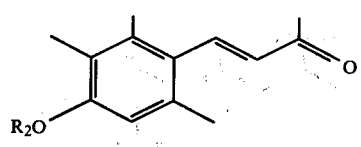
IX where the dotted line is as above;

with a Grignard reagent, followed by treatment with a halogenating agent and finally with a sulfinic acid. The sulfonation reaction is carried out at a temperature ranging from about −50° C. to about 150° C., preferably 0° C. to 25° C. and at atmospheric pressure. The reactions are carried out in the presence of a conventional aprotic solvent.

Compounds VIII and IX are treated with a vinylmagnesium halide and reacted under conventional Grignard conditions. Vinylmagnesium chloride is the preferred Grignard. The reaction takes place in an ether solvent. Typical ethers that may be employed are diethyl ether, dioxane and tetrahydrofuran (THF). THF is generally preferred. The ratio of Grignard to compound VIII or IX is not critical. Molar ratios of Grignard to compound VIII or IX of 1:1 are generally employed.

The resulting alcohol is then treated with a conventional halogenating agent, e.g., a thionyl halide or a phosphorus trihalide or hydrogen halide in the presence of a base. Phosphorus tribromide is the preferred halogenation agent.

The reaction temperature may vary from about −25° C. to about 25° C. The molar ratio of halogenating agent to the alcohol is not critical but ratios of about 1:1 are generally employed.

The reaction is conducted in a medium comprised of an inert solvent and an acid scavenger. Typical solvents that may be employed are diethyl ether, hexane, benzene, toluene and the like. Typical scavengers that may be employed are lower alkyl primary, secondary and tertiary amines, aromatic amines, heterocyclic amines. Pyridine is particularly preferred.

The resulting halide is then reacted with an alkali metal salt of a sulfinic acid of the formula

Z—SO$_2$R$_5$  X wherein Z is an alkali metal and R$_5$ is as above to form a sulfone of formula V-A or V-B.

This reaction is conducted in a polar solvent at atmospheric pressure and at a temperature ranging from about −25° C. to about 150° C., preferably 0° C. to 25° C.

The sulfinic acids of formula V generally employed are alkali metal salts of aryl sulfinic acids with sodium phenyl sulfinate being preferred. Other sulfinic acid salts that may be employed are those where R$_5$ is alkyl, aryl, lower alkyl-aryl. Alicyclic and heterocyclic sulfinic acids may also be used. The molar ratio of sulfinic acid to the halide is not critical. Generally, molar ratios of about 1:1 are generally employed.

The polar aprotic solvents generally employed are dimethylformamide (DMF), dimethylacetamide, dimethylsulfoxide, (DMSO), hexamethylphosphoramide, or N-methyl-pyrrolidone.

A sulfone of the formula

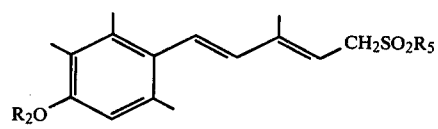
V-B wherein R$_2$ and R$_5$ are as above is novel and provides an additional aspect of this invention. A preferred species of compound V-B is one where R$_2$ is methyl and R$_5$ is phenyl.

The corresponding sulfones of compounds V-C and V-D may be prepared in accordance with the foregoing procedures to produce acyclic sulfones. Typical sulfones contemplated are those having the formulas:

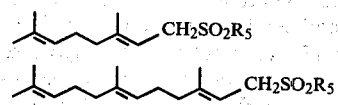
V-C

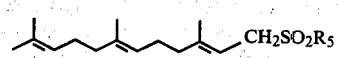
V-D wherein R$_5$ is as above.

It is to be understood that although geranyl sulfones (V-C) and farnesyl sulfones (V-D) are illustrated, sulfones of acyclic terpenes having up to 40 carbon atoms may be prepared by the foregoing procedures. Typical of the acyclic sulfones that may be prepared are those disclosed in Julia, U.S. Pat. No. 3,781,313 and Chabardes et al. U.S. Pat. No. 3,803,252, the disclosures of both are incorporated herein by reference.

Compounds corresponding to formulae IV and V are reacted to form compounds I, II or III in accordance with the following sequence:

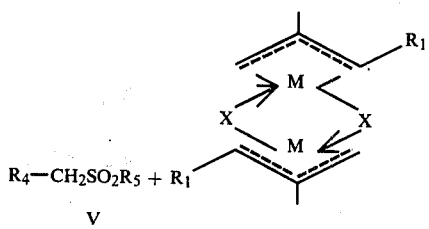
IV

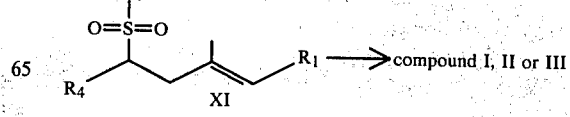
XI
⟶ compound I, II or III wherein MR$_1$, R$_4$ and R$_5$ are as above.

The reaction between compounds IV and V to form compound XI is conducted in an aprotic solvent under basic conditions in the presence of a ligand or a solvent capable of coordinating with the transition metal. The reaction is carried out at atmospheric pressure and a temperature of from about −25° C. to about 25° C.

Typical bases that may be employed are alkali metal hydrides or alkoxides, wherein the alkyl moiety is lower alkyl, and alkali metal amides wherein the alkyl moiety is lower alkyl. A preferred base is sodium hydride.

Among the aprotic solvents that may be employed are DMF, DMSO, dimethylacetamide, hexamethylphosphoramide and N-methylpyrrolidone. DMF is a preferred solvent.

Among the ligands that may be employed are the optically active or inactive mono- di- or tri-substituted phosphines, amines and arsines. The substituents may be lower alkyl, aryl, lower alkyl-aryl moieties. The preferred ligands are the fully substituted optically inactive species. Particularly preferred is triphenylphosphine. It is essential that the ligand be present in order that compound XI be formed. Not wishing to be bound by any particular theory, it is believed that the presence of the ligands causes compound IV to retain its planarity, thus enabling the formation of compound XI to occur. The amount of ligand required may vary from about 0.001 mole to about 4 moles, preferably about 0.005 mole is employed.

In lieu of the aforementioned ligands, solvents such as DMSO and hexamethylphosphoramide may be employed. The use of these reagents provides an attractive alternative in that the aforementioned solvents are also within the class of solvents in which the above reaction takes place.

Compounds of the formula XI are novel and form an additional aspect of this invention.

Exemplary of the compounds of formula XI are those of the formulas:

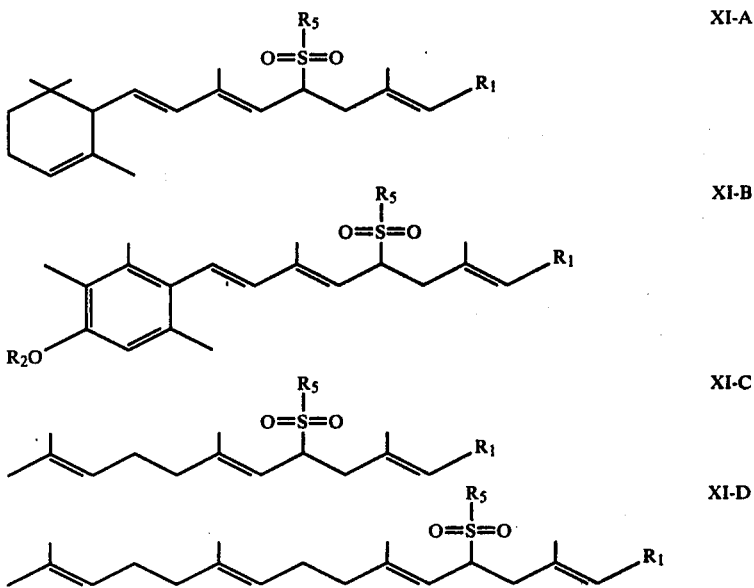

wherein $R_1$, $R_2$ and $R_5$ are as above.

Preferred species of compounds XI-A to XI-D are those wherein $R_1$ is

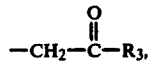

where $R_3$ is methyl, $R_2$ is methyl and $R_5$ is aryl, particularly phenyl. It is also to be understood that although in formulas XI-C and XI-D geranyl and farnesyl type compounds are illustrated, analogous acyclic terpenes having up to 40 carbon atoms are preparable according to the foregoing procedure.

Compound XI is then treated with either alkali metal alkoxides or a mixture of a lower alkanol and an alkali metal hydroxide to form a compound of formula I, II or III where $R_1$ is —CH$_2$—OH. If an alkali metal alkoxide is employed, the reaction is carried out in a lower alkanol solvent. If an alkali metal hydroxide is employed in conjunction with a lower alkanol, the latter acts as the solvent. The reaction is carried out at atmospheric pressure and at a temperature ranging from about 0° C. to about 100° C.

The following compounds of the foregoing reaction are typical of the acyclic products produced thereby:

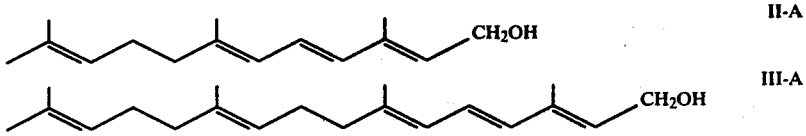

The foregoing acyclic compounds are useful as colorants. The corresponding aromatic and cyclohexenyl compounds of formula I are well known in the vitamin field. Compound I, where R is

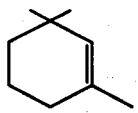

and $R_1$ is —$CH_2OH$, is vitamin A alcohol.

The following non-limiting examples are provided to illustrate the instant invention. All experiments involving polyenes were carried out in subdued light and in an inert atmosphere. All temperatures are in degrees Centigrade.

EXAMPLE 1

Preparation of π-Allyl Complex

To a 3-necked 1 liter round-bottomed flask equipped with a mechanical stirrer, addition funnel, condenser, thermometer and an argon inlet tube (a Y adapter was used) were added 24.0 g. (0.293 M) sodium acetate (anhydrous), 16.7 g. (0.288 M) sodium chloride, 23.4 g. (0.1037 M) cupric chloride, 4.0 g. (0.0226 M) palladium (II) chloride, 250 ml. of acetic acid and 5.0 ml. of acetic anhydride. The mixture was stirred at 95° for 2 hours, cooled to 60° and then treated with 6.65 g. (0.05 M) of prenyl acetate [prepared from prenol and acetic anhydride-triethylamine (in hexane 25° for 3 hours)] in 15 ml. of acetic acid. The mixture was stirred at 85° for 2 hours, cooled to room temperature, filtered through celite and the filter pad washed with two 75-ml. portions, a total of 150 ml. of acetic acid. Evaporation of the solvent in vacuo gave an orange-colored oil. The latter was extracted into three 1-l portions, a total of 3 liters of benzene, washed with saturated brine, dried over $MgSO_4$ and evaporated to give 9.6 g. of crude π-allyl complex. This was dissolved in chloroform and chromatographed on 100 g. of silica gel with chloroform as eluent, which upon evaporation yielded the π-allyl complex as pale yellow crystals. Repeated crystallizations from methylene chloride-hexane gave 5.3 g. of an analytical sample, m.p. 155°–159°.

Analysis Calcd. for $C_{14}H_{22}O_4Cl_2Pd_2$: C, 31.25; H, 4.12; Cl, 13.18; Pd, 39.55. Found: C, 31.03; H, 3.97; Cl, 13.28; Pd, 39.40.

EXAMPLE 2

Conversion of α-Ionone into the C-15 Sulfone (a) Preparation of Vinyl α-Ionol To a 3-necked 1 liter round-bottomed flask equipped with a mechanical stirrer, addition funnel, thermometer and an argon-inlet tube was added 28.75 g. (0.15 M) of α-ionone (freshly distilled through a 1 ft. Vigreau column, b.p. 97°/1.3 mmHg) in 300 ml. of anhydrous THF. The mixture was cooled to −50° and treated with 61.5 ml. (0.18 M) of a 2.93 M solution of vinyl magnesium chloride in THF at such a rate that the temperature was ca. −50°. The mixture was stirred at −50° for 3 hours, treated with 200 ml. of saturated ammonium chloride, poured into 500 ml. of water and extracted with two 250 ml. portions, a total of 500 ml. of ether. The extract was washed with saturated brine, dried over $MgSO_4$ and evaporated. Distillation gave 20.3 g. of vinyl α-ionol, b.p. 105°–108°/1.2 mm.

(b) Preparation of the C-15 Sulfone

To a 500 ml. 3-necked round-bottomed flask equipped with a mechanical stirrer, addition funnel, condenser, argon inlet and a thermometer was added 16.5 g. of vinyl α-ionol (from part (a) of this example) in 150 ml. of anhydrous ether and 15 ml. of pyridine. The mixture was cooled to −15° and treated with 31.5 g. of phosphorus tribromide in 50 ml. of ether during 30 minutes at such a rate that the internal temperature was kept at ca. −10°. The mixture was stirred at 0° for 3 hours, cooled to −20°, treated dropwise with 100 ml. of water and then poured into a separatory funnel containing 200 ml. of water and 200 ml. of ether. The organic phase was separated, washed with three 350 ml. portions, a total of 1.05 liter of saturated brine, dried over $MgSO_4$ and evaporated to give a pale yellow oil which was dissolved in 100 ml. of DMF and then treated with 24.0 g. of phenyl sulfinic acid (sodium salt, Aldrich, 98%). The mixture was stirred at 25° overnight, poured into a separatory funnel containing 400 ml. of water and 200 ml. of ether. The organic phase was separated and the aqueous phase re-extracted with 200 ml. of ether. The combined extracts were washed with three 300 ml. portions, a total of 900 ml. of saturated brine, dried over $MgSO_4$ and evaporated to give 16.8 g. of a viscous oil which was shown by thin layer chromatography to be a mixture of four compounds having Rf 0.98, 0.70, 0.60 and 0.56. A portion (500 mg.) of this material was subjected to preparative scale thin layer chromatography and collection of the material at Rf 0.56 followed by crystallization from methanol (−10° overnight) gave pure vinyl α-ionyl sulfone, m.p. 68°–69°. The rest of the material (16.3 g.) was then subjected to column chromatography on 1 kg. of neutral alumina (Woelm, Grade I) first with 5% ethyl acetate in hexane followed by 10% ethyl acetate in hexane which eluted essentially pure vinyl α-ionyl sulfone (ascertained by thin layer chromatography). Evaporation of the solvents gave an oil which was dissolved in 20 ml. of methanol, cooled to −20° and seeded with a few mgs. of crystalline material (obtained above) and left at −15° overnight. The crystals were filtered, washed with 50 ml. of cold (−15°) methanol followed by 25 ml. of cold (−15°) hexane and dried in vacuo to give 8.0 g. of pure vinyl α-ionyl sulfone, m.p. 69°–70.5°.

Analysis Calcd. for $C_{21}H_{28}O_2S$: C, 73.21; H, 8.19; S, 9.31. Found: C, 73.33; H, 7.98; S, 9.10.

EXAMPLE 3

Reaction of vinyl α-ionyl sulfone with the π-allyl complex

To a 50 ml. 3-necked round-bottomed flask equipped with an addition funnel, thermometer, nitrogen inlet tube and containing a magnetic stirrer bar was added 344 mg. (0.001M) of vinyl α-ionyl sulfone in 20 ml. of anhydrous DMF. The solution was cooled to −10°, treated with 47.8 mg. of sodium hydride (obtained by washing 84 mg. of 57% material), and stirred at −10° for 10 minutes. To the red solution was added 1.04 g. (0.004M) of triphenyl phosphine followed after 10 minutes at 0° by 260 mg. of the pure π-allyl complex of Example 1 in 10 ml. of DMF. Within a few minutes a yellow precipitate was deposited. The mixture was stirred at 0° for 45 minutes (thin layer chromatography indicated that the reaction was virtually complete after 30 minutes) and then filtered through a pad of celite. The pad was washed with 80 ml. of ether, the filtrate and washings were combined, poured into a separatory funnel and diluted with 200 ml. of water. The organic phase was separated and the aqueous phase re-extracted with 150 ml. of ether. The combined extracts were washed with three 200 ml. portions, a total of 600 ml. of saturated brine, dried over MgSO$_4$ and evaporated. Thin layer chromatography indicated the presence of three compounds: phenylphosphine (Rf 0.70), product (Rf 0.32), hydrolyzed product (Rf 0.13); the starting material has Rf 0.40. Preparative scale thin layer chromatography, followed by extraction into methylene chloride and evaporation, gave a gum. The latter was kept in vacuo (1.0 mm) overnight to give 230 mg. of pure 3,7-dimethyl-5-phenylsonfonyl-9-(2,6,6-trimethyl-cyclohexen-2-yl)-2,6,8-nonatriene acetate (α-C 20 sulfone) as a gum which failed to crystallize.

Analysis Calculated for C$_{28}$H$_{38}$O$_4$S: C, 71.45; H, 8.14; S, 6.81. Found: C, 71.24; H, 8.04; S, 6.80.

EXAMPLE 4

Reaction of π-allyl complex with vinyl β-ionyl sulfone

The vinyl β-ionyl sulfone was prepared in a manner similar to that of Example 2 with the exception that the starting material was β-ionone.

To a 3-necked 100-ml. round-bottomed flask equipped with a magnetic stirrer, addition funnel and an argon-inlet tube was added 168 mg. (0.004M) of sodium hydride (57%) to 35 ml. of anhydrous DMF. The mixture was cooled to. −10° and treated with 1.37 g. (0.004M) of vinyl β-ionyl sulfone in 10 ml. of DMF. Stirring was continued for a further 15 minutes and the resulting deep red solution was cooled to −20° and treated with 4.16 g. (0.016M) of triphenyl phosphine, followed by 1.076 g. (0.002M) of the pure π-allyl complex of Example 1 in 20 ml. of DMF. A pale yellow solid precipitated from the reaction mixture after ca. 15 minutes. The mixture was stirred at −10° for 2 hours and then at 0° for 1 hour, filtered through celite and the filtrate diluted with 200 ml. of saturated brine. The mixture was extracted with three 150 ml. portions, a total of 450 ml. of ether, dried with MgSO$_4$ and evaporated to give a reddish brown gum. Thin layer chromatography analysis showed two main spots: product (Rf 0.34) and triphenyl phosphine (Rf 0.44), with a small amount of hydrolyzed product at Rf 0.15.

Preparative scale thin layer chromatography, collection of the band at Rf 0.34, followed by extraction into methylene chloride, filtration and evaporation gave 680 mg. of pure 3,7-dimethyl-5-phenylsulfonyl-9-(2,6,6-trimethylcyclohexen-1-yl)-2,6,8-nonatriene acetate (β C-20 sulfone).

Analysis Calcd. for C$_{28}$H$_{38}$O$_4$S: C, 71.45; H, 8.14; S, 6.81. Found: C, 71.61; H, 8.22; S, 6.90.

EXAMPLE 5

Conversion of β-C-20 sulfone into vitamin A acetate

Into a 1 liter, 3-necked round-bottomed flask equipped with a condenser, mechanical stirrer and nitrogen inlet was added 270 ml. of ethanol (200 proof) followed by 12.3 g. of clean sodium in small pieces. After all the sodium had reacted (heating was applied to complete the reaction), 25.3 g. of the β-C$_{20}$ sulfone in 100 ml. of ethanol (warming required) was added. The deep red solution was boiled under reflux for 17 hours, cooled to room temperature and added to a separatory funnel containing 500 ml. of ether and 500 ml. of saturated brine. The organic phase was separated and the aqueous phase was re-extracted with 400 ml. of ether. The combined extracts were washed with three 500 ml. portions, a total of 1.5 liter of saturated brine, dried over MgSO$_4$, evaporated and then kept in vacuo to give 18.6 g. of a viscous orange colored oil. About 100 mg. of butylated hydroxy toluene was added followed by 300 ml. of hexane and 13.5 ml. of pyridine. To the stirred solution was added 45.3 ml. of acetic anhydride. The mixture was stirred at room temperature for 3½ hours, treated dropwise with 100 ml. of methanol, stirred for an additional hour and then added to a separatory funnel containing 400 ml. of water. The organic phase was separated and the aqueous phase re-extracted with 400 ml. of hexane. The extracts were washed with 600 ml. of ice cold 0.1N sulfuric acid and then twice with 600 ml. of water, a total of 1.2 liter of water. The organic phase was dried over MgSO$_4$ and evaporated to give 17.8 g. of an orange colored gum. Thin layer chromatography showed no separation with an authentic sample of all trans vitamin A acetate (Rf 0.64); trace impurities were observed at 0.69, 0.26, 0.19 and 0.13. LC analysis gave the following results: all-trans 67%, 9/9,13-dicis 9%, 13-cis 1%, 11-cis 1%, retro 2%: total 80%.

EXAMPLE 6

Preparation of α-vitamin A

To a 3-necked 25 ml. round-bottomed flask equipped with a condenser, argon inlet and containing a magnetic stirrer was added 62 ml. of the α C-20 sulfone of Example 3 in 5 ml. of n-butanol. 480 mg. of potassium hydroxide (85%, pulverized) was added and the resulting darkcolored solution boiled under reflux for 16 hours, diluted with 50 ml. of water and extracted into 50 ml. of ether. The extract was washed with two 50 ml. portions, a total off 100 ml. of saturated brine, dried over MgSO$_4$ and evaporated to yield the product as a pale yellow gum (45 mg.).

EXAMPLE 7

Preparation of aromatic C-15 sulfone (a) Reaction of vinyl magnesium chloride with the ketone To a 3-necked 500 ml. round-bottomed flask equipped with a mechanical stirrer, addition funnel, argon inlet tube and a thermometer was added 5.45 g. of 1-(2,5,6-trimethyl-4-methoxyphenyl)-but-1-en-3-one in 150 ml. of anhydrous THF. The mixture was cooled to −60° and treated dropwise with 10.25 ml. of a 2.93M solution of vinyl magnesium chloride in 50 ml. of THF. The mixture was then stirred at −60° for 3 hours, quenched with 100 ml. of saturated ammonium chloride, poured into a separatory funnel and extracted with two 150 ml. portions, a total of 300 ml. of ether. The organic phase was washed with three 300 ml. portions of saturated brine, dried over MgSO$_4$ and evaporated to give the corresponding vinyl alcohol as an oil which was kept in vacuo until a constant weight was attained: yield 7.5 g. (tlc indicated a product having Rf 0.36).

(b) Conversion of the vinyl alcohol into the sulfone

To a 3-necked 100 ml. round-bottomed flask equipped with an argon inlet tube and containing a magnetic stirrer bar was added 5.0 g. of the preceding vinyl alcohol, followed by 30 ml. of acetic acid (a transient green color was obtained). To the stirred solution was added 7.0 g. of benzene sulfinic acid (sodium salt, Aldrich). The mixture was stirred at room temperature for 5 hours, poured into 300 ml. of water, extracted into two 200 ml. portions of ether, washed with four 400 ml. portions of water, dried over MgSO$_4$ and evaporated to give 6.1 g. of an oil. This was dissolved in 15 ml. of methanol, left at −15° overnight and filtered to give 3.4 g. of crude 5-(2,5,6-trimethyl-4-methoxyphenyl)-3-methyl-penta-2,-4-dienylphenylsulfone. 1.5 G. of this material was dissolved in 15 ml. of hot methanol, left at 0° overnight and filtered. The crystals were washed with 10 ml. of cold (−15°) methanol to give 1.1 g. of pure sulfone, m.p. 117°-118°.

EXAMPLE 8

Reaction of sulfone with π-allyl complex

To a 3-necked 25 ml. round-bottomed flask equipped with a thermometer, argon inlet tube, addition funnel and containing a magnetic stirrer bar was added 130 mg. of the sulfone of Example 7 in 10 ml. of anhydrous DMF. The mixture was cooled to 10° and treated with 26 mg. of sodium hydride (57%). A deep red solution resulted. The mixture was stirred for 3 minutes (cooling removed), treated with 370 mg. of triphenyl phosphine, stirred for an additional 3 minutes at room temperature and then treated with 95 mg. of the pure π-allyl complex of Example 1. The deep red solution changed to pale yellow with the deposition of a precipitate. The mixture was stirred at room temperature for 45 minutes, filtered through celite, the latter washed with 50 ml. of ether. The filtrate and washing were diluted with 50 ml. of water and the organic phase separated. The aqueous phase was re-extracted with 50 ml. of ether and the combined extracts were washed with two 100 ml. portions, a total of 200 ml. of water, dried over MgSO$_4$ and evaporated to give a gum. (Tlc showed that the product has Rf 0.70 and the starting material Rf 0.75). The crude product was subjected to preparative scale thin layer chromatography, collection of the main band (Rf 0.70), extraction into methylene chloride, filtration and evaporation gave 68 mg. of 3,7-dimethyl-5-phenylsulfone-9-(2,5,6-trimethyl-4-methoxyphenyl)-2,6,8-nonatriene acetate (aromatic C-20 sulfone).

Microanalysis Calcd. for $C_{29}H_{36}O_5S$: C, 70.13; H, 7.31; S, 6.45. Found: C, 69.92; H, 7.56; S, 6.35.

EXAMPLE 9

Conversion of aromatic C-20 sulfone into the aromatic vitamin A analogue

To a 25 ml. 3-necked round-bottomed flask equipped with a condenser, argon inlet tube and containing a magnetic stirrer bar was added 5 ml. of absolute ethanol followed by 97 mg. of clean sodium. After all the sodium had reacted (warming necessary), 100 mg. of the aromatic C-20 sulfone in 3.0 ml. of ethanol was added to the warm solution. The stirred mixture was boiled under reflux for 12 hours, cooled to room temperature and poured into 50 ml. of water. The mixture was extracted with two 50 ml. portions, a total of 100 ml. of ether, washed with water until neutral, dried over MgSO$_4$ and evaporated to give a red oil to which a few crystals of BHT were added. Preparative scale thin layer chromatography (a product having Rf 0.60 and starting material Rf 0.80) indicated 40 mg. of 9-(2,5,6-trimethyl-4-methoxyphenyl)-3,7-dimethyl-2,4,6,8-nonatetraene-1-ol as an amorphous solid, m.p. 114°-121°.

EXAMPLE 10

Reaction of geranyl phenyl sulfone with π-allyl complex

To a 3-necked round-bottomed flask equipped with a thermometer, addition funnel, argon inlet tube and containing a magnetic stirrer bar was added 278 mg. of geranyl phenyl sulfone in 20 ml. of anhydrous DMF. The mixture was cooled to 0° and treated with 84 mg. of sodium hydride (57%) to give a deep red anion which was stirred for a further 5 minutes. 1.04 G. of triphenyl phosphine was added, and after 15 minutes 270 mg. of π-allyl complex of Example 1 in 15 ml. of anhydrous DMF was added. The mixture was stirred at room temperature for 2 hours, filtered through celite and washed with 25 ml. of ether. The filtrate and washing were diluted with 45 ml. of water and 50 ml. of ether. The organic phase was separated, washed with three 50 ml. portions, a total of 150 ml. of water, dried over MgSO$_4$ and evaporated to give a gum. Thin layer chromatography indicated starting material having Rf 0.37 and product Rf 0.30. Preparative scale thin layer chromatography gave 85 mg. of 3,7,11-trimethyl-5-phenylsulfone-2,6,10-dodecatriene acetate (acyclic C-15 sulfone) as a gum.

EXAMPLE 11

Conversion of the acyclic C-15 sulfone into 7,8-dehydro-farnesyl acetate

To a 3-necked 100 ml. round-bottomed flask equipped with a condenser capped with an argon inlet tube, and containing a magnetic stirrer bar was added 220 mg. of the sulfone of Example 11 in 15 ml. of n-butanol. 1.5 G. of KOH (pulverized) was added and the mixture boiled under reflux for 30 minutes. The mixture was cooled to room temperature, poured into 50 ml. of water and extracted with two 50 ml. portions, a total of 100 ml. of ether. The extract was washed with two 50 ml. portions, a total of 100 ml. of saturated brine, dried over MgSO$_4$, evaporated and then kept in vacuo until a constant weight was obtained. Thin layer chromatography showed that the product has Rf 0.45 and starting material Rf 0.45; the corresponding hydrolyzed sulfone has Rf 0.23. The crude product above was dissolved in 5 ml. of hexane, added to a 25 ml. 3-necked round-bottomed flask under argon, treated with 1.0 ml. of pyridine followed by 4.0 ml. of acetic hydride and stirred at room temperature for 1 hour. The solution was cooled to 0°, treated dropwise with 10 ml. of methanol, stirred at room temperature for 15 minutes and then poured into 50 ml. of water and diluted with 50 ml. of hexane. The organic phase was separated, washed with three 50 ml. portions, a total of 150 ml. of brine, dried over MgSO$_4$ and treated with a few crystals of butylated hydroxytoluene. Filtration and evaporation gave a gum which was subjected twice to preparative scale thin layer chromatography and gave 7,8-dehydro-farnesyl acetate as an oil.

Microanalysis Calcd. for $C_{17}H_{26}O_2$: C, 77.81; H, 9.99. Found: C, 77.86; H, 9.95.

EXAMPLE 12

Preparation of farnesyl phenyl sulfone

To a 500 ml. 3-necked round-bottomed flask equipped with a condenser, mechanical stirrer, thermometer and addition funnel was added, under argon, a solution of 11.1 g. of nerolidol in 100 ml. of anhydrous ether. The solution was cooled to −10° and treated with 21 g. of phosphorus tribromide in 40 ml. of ether at such a rate that the internal temperature was kept at ca. −5° (15 minutes). Stirring was continued at 0°-5° for 2¼ hours, cooled to −5° and treated dropwise with 40 ml. of water (internal temperature kept below 20°). The mixture was poured into 75 ml. of water, the organic phase was separated and the aqueous phase re-extracted with 150 ml. of ether. The combined extracts were washed with 150 ml. of saturated brine, 150 ml. of saturated sodium bicarbonate, followed by two 150 ml. portions, a total of 300 ml. of saturated brine, dried over MgSO$_4$ and evaporated to give 11.0 g. of farnesyl bromide. The preceding crude farnesyl bromide was dissolved in 110 ml. of DMF, treated with 15 g. of phenyl sulfinic acid (sodium salt, 96%) and the resulting heterogeneous mixture stirred under nitrogen for 20 hours at room temperature. The mixture was poured into 300 ml. of water, extracted with two 150 ml. portions, a total of 300 ml. of ether, washed with three 300 ml. portions, a total of 900 ml. of saturated brine, dried over MgSO$_4$ and evaporated to give 11.7 g. of a pale yellow oil. Thin layer chromatography indicated the following spots: Rf 0.83 (by-product), 0.60 (by-product), 0.46 (product). The crude product was dissolved in 10 ml. of 20% ethyl acetate in hexane and chromatographed on 300 ml. of neutral alumina (Woelm Grade II, dry pack, 1½" diameter column) with 20% ethyl acetate in hexane as eluent (15 ml. fractions, monitored by thin layer chromatography) to give 8.4 g. of farnesyl phenyl sulfone as an oil. Rf of product 0.47. Preparative scale thin layer chromatography of a 500 mg. portion gave an analytical sample.

Analysis Calcd. for $C_{21}H_{30}O_2S$: C, 72.79; H, 8.73; S, 9.29. Found: C, 72.71; H, 8.81; S, 9.11.

EXAMPLE 13

Reaction of farnesyl phenyl sulfone with $\pi$-allyl complex

To a 3-necked 50 ml. round-bottomed flask equipped with a dropping funnel, argon inlet tube and containing a magnetic stirrer bar was added 346 mg. of farnesyl phenyl sulfone in 10 ml. of anhydrous DMF. The mixture was cooled to 0°, treated with 84 mg. of sodium hydride (57% dispersion), stirring was continued at 0° for 10 minutes and the mixture treated with 1.04 g. of triphenylphosphine. The mixture was treated after 5 minutes with 280 mg. of the pure $\pi$-allyl complex of Example 1 in 20 ml. of anhydrous DMF, stirred at 0° for 30 minutes and then at room temperature for a further 30 minutes. The heterogeneous mixture was filtered through celite, which was washed with 50 ml. of ether, the washing and filtrate were diluted with 100 ml. of water and the organic phase collected. The aqueous phase was re-extracted with 100 ml. of ether and the combined extracts washed with three 100 ml. portions, a total of 300 ml. of brine, dried over MgSO$_4$ and evaporated to give a gum. Thin layer chromatography showed the following spots: product Rf 0.51, by-product Rf 0.77 and triphenylphosphine 0.83; the starting material has Rf 0.60. Preparative scale thin layer chromatography, collection of the product by extraction into methylene chloride, filtration and evaporation gave 93 mg. of 3,7,11,15-tetramethyl-5-phenylsulfone-2,6,10,14-hexadecatetraene acetate (acyclic C-20 sulfone).

Analysis Calcd. for $C_{28}H_{40}O_4S$: C, 71.15; H, 8.53; S, 6.78. Found: C, 71.00; H, 8.50; S, 6.67.

EXAMPLE 14

Conversion of the acyclic C-20 sulfone into 7,8-dihydro-$\gamma$-vitamin A acetate To a 3-necked 50 ml. round-bottomed flask equipped with a condenser, argon inlet and containing a magnetic stirrer bar was added a solution of 1.0 g. of the sulfone of Example 13 in 20 ml. of n-butanol. 1.13 G. of KOH (pulverized) was added, the mixture boiled under reflux for 2½ hours, cooled to room temperature, poured into 100 mg. of water and extracted with 100 ml. of ether. The extract was washed with four 100 ml. portions, a total of 400 ml. of brine, dried over MgSO$_4$ and evaporated (traces of n-butanol were removed by azeotroping with cyclohexane) to give 600 mg. of an oil (thin layer chromatography showed product at Rf 0.43 and starting material at 0.50). This was dissolved in 20 ml. of hexane and 4 ml. of triethylamine followed by 4 ml. of acetic anhydride. The mixture was stirred under argon for 3 hours, cooled to 0°, treated dropwise with 10 ml. of methanol and then stirred for a further 30 minutes. The solution was poured into 100 ml. of water, extracted twice with 100 ml. of hexane (a total of 200 ml.), washed with 200 ml. of saturated brine, dried over MgSO$_4$ and evaporated to give an oil: thin layer chromatography indicated product Rf 0.74, small by-products at Rf 0.86 and Rf 0.60; the starting material has Rf 0.36. Preparative scale thin layer chromatography followed by extraction, filtration and evaporation gave 580 mg. of the product as an oil.

Analysis Calcd. for $C_{22}H_{34}O_2$: C, 79.95; H, 10.37. Found: C, 79.48; H, 10.41.

I claim:

1. A process for the preparation of a compound of the formula

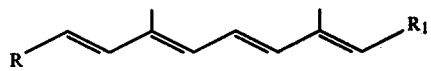

wherein
R is

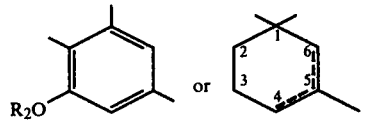

$R_1$ is —CH$_2$OH, or

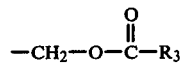

$R_2$ and $R_3$ are lower alkyl the dotted line is a carbon-carbon bond which may be in either the 4,5 or 5,6 position;
which comprises reacting a compound of the formula

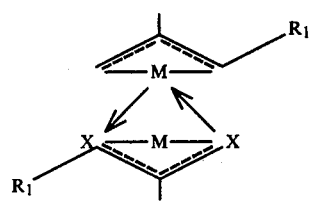

wherein M is Pd or Pt, X is halogen;
with a compound of the formula

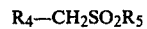

wherein R₄ is

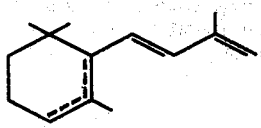

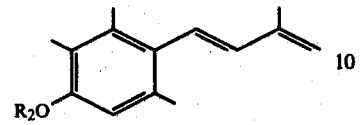

and

R₅ is lower alkyl, aryl or lower alkylaryl and the dotted line is a carbon to carbon bond in either the 4,5 or 5,6 position;

under basic conditions in the presence of a ligand or a solvent capable of coordinating with the platinum or palladium to form a compound having the formula

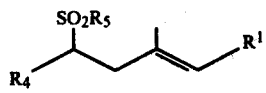

wherein R₁, R₄ and R₅ are as defined above followed by treatment of said compound with a base.

2. The process of claim 1 wherein R₄ is

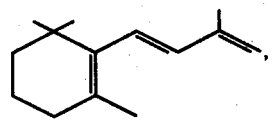

R₅ is phenyl, M is Pd and the halogen is chlorine.

3. The process of claim 2 wherein the reaction is conducted in the presence of an optically inactive ligand.

4. The process of claim 3 wherein said ligand is triphenylphosphine.

5. The process of claim 1 wherein said base is an alkali metal alkoxide.

6. The process of claim 5 wherein said alkali metal alkoxide is sodium ethoxide.

7. The process of claim 1 wherein R₄ is

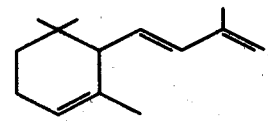

R₅ is phenyl, M is Pd and the halogen is chlorine.

8. The process of claim 7 wherein the reaction is conducted in the presence of an optically inactive ligand.

9. The process of claim 8 wherein said ligand is triphenylphosphine.

10. The process of claim 1 wherein R₄ is

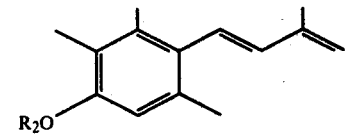

R₂ is methyl, R₅ is phenyl, M is Pd and the halogen is chlorine.

11. The process of claim 10 wherein the reaction is conducted in the presence of an optically inactive ligand.

12. The process of claim 11 wherein said ligand is triphenylphosphine.

13. A process for the preparation of a compound of the formula

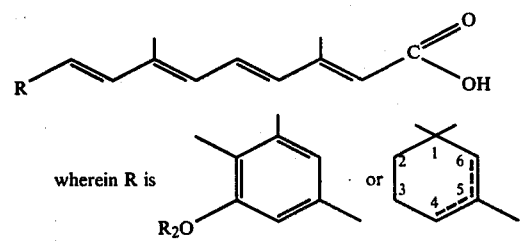

wherein R is and

R₂ is lower alkyl; the dotted line is a carbon-carbon bond which may be in either the 4,5 or 5,6 position;

which comprises reacting a compound of the formula

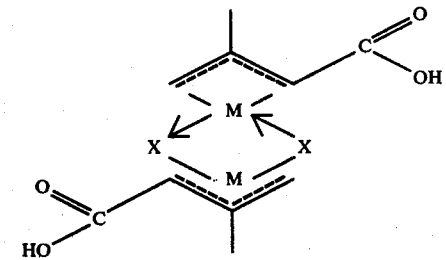

wherein M is Pd or Pt, and X is halogen; with a compound of the formula

R₄—CH₂SO₂R₅ wherein
R₄ is

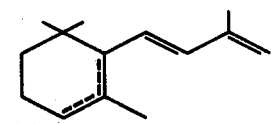

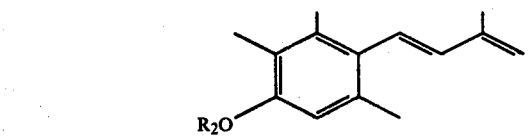

and

R₅ is lower alkyl, aryl or lower alkylaryl and the dotted line is a carbon to carbon bond in either the 4,5 or 5,6 position;

in the presence of a base selected from the group consisting of alkali metal lower alkoxides, hydrides and amides in the presence of a ligand selected from mono-, di- or tri-substituted amines, arsines, or phosphines wherein said substitutents are lower alkyl, aryl or lower alkylaryl or a solvent capable of coordinating with the platinum or palladium selected from dimethylsulfoxide or hexamethylphosphoramide to form a compound having the formula

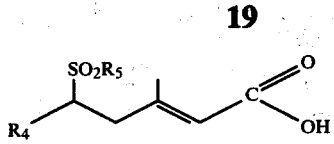
wherein $R_4$ and $R_5$ are as defined above followed by treatment of said compound with a base selected from alkali metal hydroxide or a mixture of a lower alkanol and an alkali metal hydroxide.
* * * * *